United States Patent [19]

Estrada et al.

[11] Patent Number: 5,304,174
[45] Date of Patent: Apr. 19, 1994

[54] MICROMANIPULATOR APPARATUS FOR SURGICAL LASER

[75] Inventors: Robert B. Estrada, Redwood City; David Trost, San Francisco, both of Calif.

[73] Assignee: Coherent, Inc., Santa Clara, Calif.

[21] Appl. No.: 100,722

[22] Filed: Aug. 2, 1993

Related U.S. Application Data

[62] Division of Ser. No. 841,427, Feb. 26, 1992, Pat. No. 5,207,380.

[51] Int. Cl.⁵ .............................................. A61B 17/36
[52] U.S. Cl. ...................................... 606/18; 403/365; 403/120
[58] Field of Search ................. 403/365, 114, 120, 82; 464/92, 51; 606/18

[56] References Cited

U.S. PATENT DOCUMENTS

| | | | |
|---|---|---|---|
| 2,706,126 | 4/1955 | Thiry | 403/365 X |
| 2,910,314 | 10/1959 | Klein | 403/365 X |
| 4,129,394 | 12/1978 | Eichinger et al. | 403/120 X |
| 4,194,850 | 3/1980 | Cranmore | 403/365 X |
| 4,229,839 | 10/1980 | Schwiemmer | 403/120 X |

Primary Examiner—Peter A. Aschenbrenner
Attorney, Agent, or Firm—Limbach & Limbach

[57] ABSTRACT

An improved apparatus for manually manipulating a surgical laser beam is disclosed. The preferred embodiment of the invention includes a mirror nominally positioned at a 45 degree angle to the incident laser beam, a joy stick for manipulating the mirror, and a linkage interconnecting the two. The mirror is mounted to allow it to rotate about two mutually perpendicular and intersecting axes. The linkage operates to direct the reflected laser beam in two orthogonal dimensions such that a ratio between the movement of the reflected beam in each dimension is equivalent to the ratio of the movement of the joy stick in each dimension. This yields a reflected laser beam that moves a distance proportional to the amount of motion input to the joy stick. The reduction or amplification ratio between the input motion and the reflected laser beam motion remains constant, regardless of the direction of motion. In this manner, by moving the joy stick in a circular motion, the reflected laser beam also moves in a circular motion, rather than in an elliptical motion. A simplified joint that allows spherical rotation and axial translation between its two members is also disclosed. In the preferred embodiment, an adjustable hand rest is provided that moves out of the way when not in use.

2 Claims, 3 Drawing Sheets

MICROMANIPULATOR APPARATUS FOR SURGICAL LASER

This is a divisional application of U.S. patent application Ser. No. 07/841.427, filed Feb. 26, 1991, now U.S. Pat. No. 5,207,380.

BACKGROUND OF THE INVENTION

1. Field of the Invention

The present invention relates to apparatus for accurately positioning a laser beam used during surgery, and more specifically to apparatus which uses a manually manipulated mirror to direct the laser beam to the intended target area on the patient.

2. Discussion of the Prior Art

For over fifteen years, laser energy has been used routinely in major and minor surgical procedures. Various surgical laser applications are found in such areas as plastic surgery, dermatology, ophthalmology, otolaryngology, neurological surgery, obstetrics and gynecology, gastroenterology, urology, and general surgery. These procedures typically require precise positioning of a laser beam on the tissue being operated on.

A surgical laser manipulating system currently in use is the MICROLITE manufactured by Coherent Medical Division in Palo Alto, Calif. A remote laser unit typically delivers a laser beam (or beams) to this micromanipulator through an articulated delivery arm. A set of adjustable optics are located between the articulated arm and the micromanipulator to allow the surgeon to adjust the focus of the beam. The micromanipulator system, focusing optics, and viewing optics may be mounted on a movable arm or stand to allow the surgeon to roughly position this equipment in the proper location relative to the patient.

Once the laser beam enters the micromanipulator unit, the beam is deflected by a mirror through approximately ninety degrees towards the patient's tissue that is to be operated on. The mirror is manipulated by the surgeon through a joy stick which is connected to the mirror by way of a simple linkage. The mirror is mounted in gimbals to allow it to rotate several degrees in any direction from its central position. A bracket attached to the inner frame of the mirror directly connects to a spherical joint located in the joy stick ball. For accurate positioning, the linkage reduces the motion of the joy stick so that a larger amount of movement of the joy stick is required for a smaller amount of movement of the mirror.

Only a small portion in the center of the mirror is highly reflective to visible light. This allows the surgeon to view the operation through the rest of the mirror, looking approximately parallel to the laser beam that is reflected off of the mirror. In a typical arrangement, the viewing optics are located above and to the front of the micromanipulator unit, the joy stick is angled upward from the front side of the unit, and the laser beam enters the back side of the unit through the focusing optics and exits through the bottom to the target area on the patient.

During a surgical procedure, a low-energy, visible laser beam, such as a helium-neon laser, is directed through the articulated delivery arm and focusing optics, reflected off of the mirror, and out the bottom of the micromanipulator unit. The surgeon moves the equipment into place over the patient with the aid of the low-powered beam and positions the beam on the exact spot he desires by looking through the viewing optics and moving the joy stick to manipulate the beam. When the surgeon is ready to operate, a high-powered laser beam, such as an invisible carbon dioxide beam, is activated, often by a foot switch, and the high-energy beam travels down the same optical path as the low-energy beam to the same target point. In some procedures, the joy stick may then be used to further move the target point while the high-energy beam is still activated.

This existing micromanipulator system has some shortcomings. Because of the simplicity of the linkage joining the joy stick to the mirror and because of the angle of the mirror in relation to the laser beam, the ratio of laser beam movement to joy stick movement is significantly smaller in the horizontal (left and right) direction of the joy stick than it is in the vertical (forward and back) direction. In other words, if the surgeon moves the joy stick in a circular motion, the laser beam spot on the patient will move in an elliptical path.

Another disadvantage in the existing system is the obstruction of vision caused by the linkage connecting the mirror to the joy stick. In order to get fairly linear and symmetrical motion in the vertical axis, the linkage must connect to the gimballed mirror bracket near its center. This part of the linkage and bracket cover a central portion of the mirror from top to bottom, thereby blocking some of the surgeon's view.

An additional drawback associated with this system is the occurrence of arm and hand fatigue experienced by the surgeon when operating the joy stick. The size of the housing of the micromanipulator has been made as small as possible so that it does not interfere with the patient when it is being positioned and so that the surgeon can see and reach around it. This leaves the joy stick protruding out from the unit with no way of steadying the hand for more accurate and comfortable laser positioning. To overcome this problem, various forms of hand rests have been used. However, the prior hand rests have had limited adjustability and could not be easily moved away from the front of the micromanipulator.

Also, a small amount of play or backlash can occur in the linkage because of the construction of the spherical joint connecting the joy stick and the mirror.

SUMMARY OF THE INVENTION

The present invention operates in much the same manner as the prior art, but overcomes the problems mentioned above.

Two intermediate links are utilized between the joy stick and the mirror. An even number of links is used to keep the output motion from being inverted. For example, when the joy stick is moved up and to the right, the reflected laser beam should move up and to the right, not down and to the left as would occur if only one intermediate link were used.

The first of the two links separates the motion input through the joy stick into two motions. The horizontal axis of motion (left and right) is converted into a translation along an axis and the vertical motion (forward and back) of the joy stick is converted into a rotation along the same axis. As in the prior art, the linkage reduces the amount of movement of the mirror in relation to the movement of the joy stick. Once the two axes of movement are separated, however, each may be reduced by a different amount.

The complex motion of the laser beam reflected off of the mirror in the prior art and in this invention can be studied using matrix algebra. Such a study will yield the following result: for a mirror that forms a nominal angle of 45 degrees with the laser beam, a rotation about the mirror's inclined axis that is a factor of the square root of two greater than the rotation about the horizontal axis results in equal movements in the two axes of the reflected output beam for equal movements of the joy stick in two axes. Therefore, with the small angles of mirror rotation involved with the micromanipulator system, this ratio of rotation in the two axes of the present invention causes the output beam to move in an approximately circular path when the joy stick is moved in a circular motion. This yields a much more uniform and predictable response, allowing the surgeon better control over the laser beam movement.

The second link of present invention converts the translational and rotational movements of the first link into two rotational movements and applies these to the mirror. Unlike the gimballed mirror of the prior art, the mirror of the present invention is mounted at one end by a ball joint, and is supported at its opposite end by the second link. This arrangement, like the prior art, constrains the motion of the mirror to rotation in two perpendicular axes, but, unlike the prior art, leaves the area above the mirror unobstructed, thus providing the surgeon with more viewing area of his or her intended target through the mirror, and allows the mirror to be easily removed.

To reduce backlash and provide a more uniform "feel" to the joy stick while keeping the linkage as simple and inexpensive to manufacture as possible, the present invention employs spherical motion joints between the two links and between the first link and the joy stick. Each joint comprises an o-ring slipped over a pin located in and movable in relation to a spherical recess. The o-ring pivots with the pin in the recess and is held under a uniform compression. This type of joint also allows the pin to move axially in and out of the recess as it pivots.

Another feature of the novel linkage is its inherent ability to allow the entire joy stick assembly to extend from the micromanipulator body at different preset angles without changing the kinematics of the linkage. To change the angle of the joy stick assembly, only one or two parts need to be exchanged.

An additional feature of the present invention is an adjustable support for the surgeon's hand that is able to pivot and retract out of the way, if desired. Retracting the adjustable hand rest completely out of the way allows the doctor to introduce other instruments easily. The support itself is a small wire bale that the surgeon can easily see through and reach around.

DESCRIPTION OF THE PREFERRED EMBODIMENT

Figure 1:
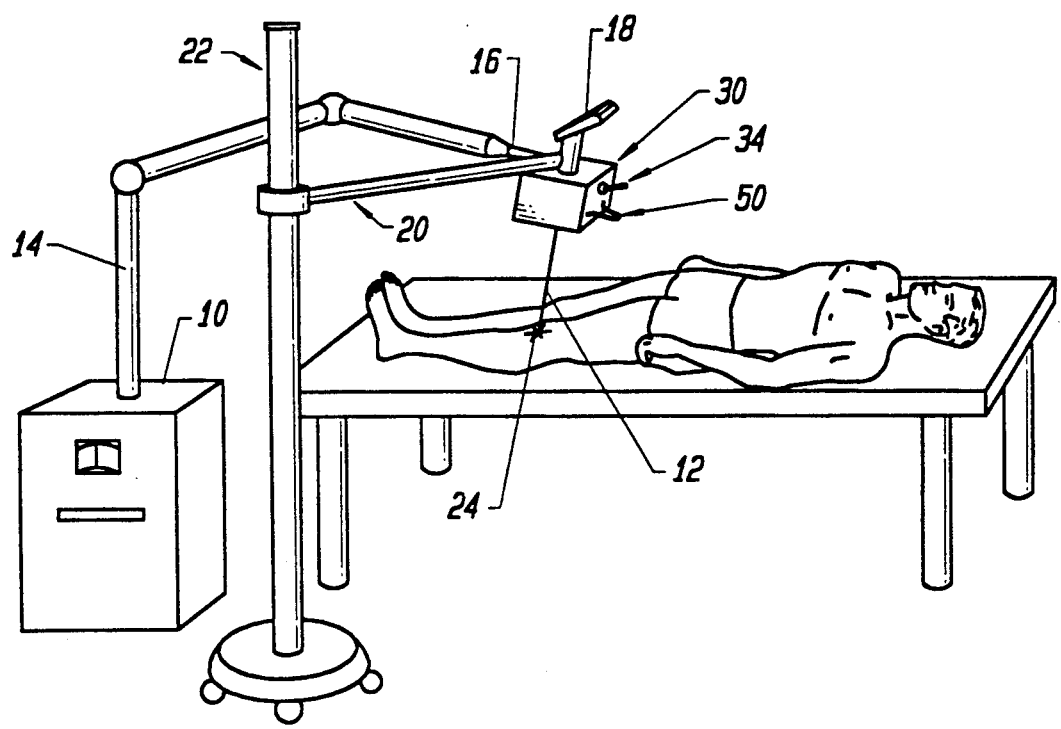
FIG. 1 is a pictorial view of the micromanipulator and the surrounding associated equipment.

FIG. 1 illustrates one possible arrangement of surgical laser equipment utilizing the micromanipulator of the present invention. A self-contained laser unit 10, includes a surgical laser and aiming beam, associated power supplies, cooling apparatus and controls, and casters to provide mobility on the hospital floor. The laser beam 12 emitted from the laser unit 10 is directed into an articulated arm 14. The articulated arm 14 is a series of hollow tubes connected by precision bearings and has mirrors at each joint for reflecting the beam 12 through the arm 14. A focusing (and defocusing) optics unit 16 is attached to the movable end of the articulated arm 14. Adjustment means, such as a lever (not shown), are provided on the focusing optics 16 to allow the surgeon to adjust the spot size, and therefore the intensity, of the laser beam 12 at the target 24. After the laser beam 12 passes through the articulated arm 14 and focusing optics 16, it travels into the micromanipulator 30, where it is reflected through roughly ninety degrees and out through the bottom of the micromanipulator 30 and onto the targeted area 24 of the patient.

The micromanipulator 30 is mounted to the underside of a microscope or viewing optics 18 by way of a band clamp or quick release adapter. The viewing optics 18 allow the surgeon to view the intended target 24 through the mirror of the micromanipulator 30 in a path approximately parallel to the reflected beam 12. The viewing optics 18, are supported by adjustable arm 20 which is movably attached to stand 22. The surgeon is able to place the laser equipment in a working position by first moving laser unit 10 and stand 22 into position and then adjusting arm 20 so that the viewing optics 18 and the micromanipulator 30 are in the proper position and orientation above the patient.

The focusing optics 16, which are supported by the micromanipulator 30, must be matched with the viewing optics 18 so that they both are focusing at the same working distance. Typical focal lengths that are available are 200, 250, 300, and 400 mm. This focal length is the distance from the objective lens (not shown) of the viewing optics 18 to the intended target 24 on the patient. The viewing optics 18 are focused by a vertical slide that moves the viewing optics 18, the micromanipulator 30, and the focusing optics 16 all as one unit with respect to the adjusting arm 20 and the patient. This keeps the beam size at the target 24 constant as the viewing optics 18 are re-focused (e.g. when moving the laser to a new target) after the beam size has been adjusted with the focusing optics 16.

Figure 2:
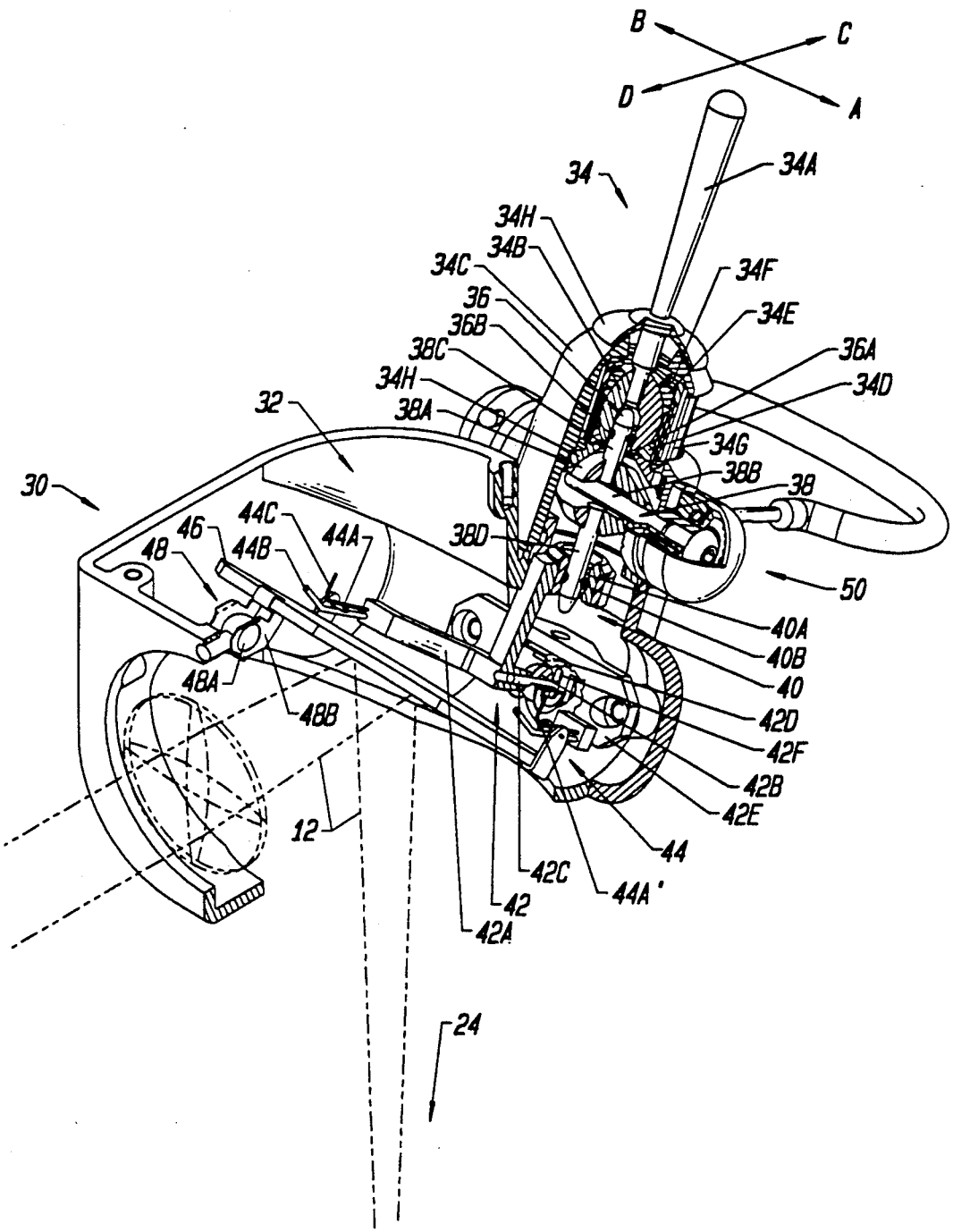
FIG. 2 is an isometric view of the micromanipulator partly in section.

Referring now to FIG. 2, the micromanipulator 30 is assembled about a micromanipulator body 32. The novel linkage that connects the motion of joy stick 34 with the mirror 46 includes a first link 38 and a second link 42. The joy stick 34 drives the first link 38 through a spherical joint 36, and the first link 38 drives the second link 42 through another spherical joint 40. The second link 42, which has a yoke 42a (only one half of the yoke 42a is shown) drives the mirror 46 through two sets of pin and clip connections 44 located at each end of the yoke 42a. The mirror 46 is mounted at its opposite end by a ball joint 48.

In the preferred embodiment of the invention, the joy stick 34 includes a handle 34a rigidly attached to a joy stick ball 34b. The ball 34b is supported from below by a ball seat 34d which is held in place by a retainer ring 34h, which in turn is threaded into a joy stick body 34c. The joy stick ball 34b is spring loaded against ball seat 34d by a load pad 34e and wave washer 34f. The spring tension may be externally adjusted by a ridged or knurled load nut 34g to set the force required to move the joy stick handle 34a. The user adjustable load nut 34g is recessed in the front of the joy stick body 34c to prevent unintentional use. The pre-load force of the wave washer 34f is applied to the ball 34b from above rather than from below to prevent the ball 34b from moving down and further compressing the wave washer 34f and moving the mirror 46 if the weight of the user's hand bears down on the joy stick handle 34a. A dust cap 34h is rigidly attached to and moves with the joy stick handle 34a to cover the entire recess in the joy stick body 34c above the ball 34b, regardless of the position of the handle 34a. This keeps fingers and foreign objects out of the way of the moving joy stick handle 34b in the recess and provides the surgeon with a surface at the bottom of the handle 34a on which to rest his lower finger(s).

The first link 38 comprises an upper pin 38c and a lower pin 38d which are rigidly mounted in a slider 38a. This assembly is constrained to slide along a main shaft 38b in a horizontal direction as shown by direction arrows A and B, and can also rotate about the main shaft 38b.

The upper pin 38c is fitted with an o-ring 36b and both are received in a recess formed in the bottom of joy stick ball 34b. A portion of this recess has a spherical wall 36a which forms the spherical joint 36 with the upper pin 38c and the o-ring 36b. The upper pin 38c and o-ring 36b move together in a pivoting motion with respect to spherical wall 36a, joy stick ball 34b, and handle 34a. As the upper pin 38c pivots out of alignment with the handle 34a, it slides through o-ring 36b and exposes more of itself outside of the recess in the ball 34b. Conversely, as the upper pin 38c pivots more into alignment with the handle 34a (towards the center position of the joy stick 34), it slides through o-ring 36b deeper into the recess in the ball 34b. To reduce backlash and hysteresis, the joint 36 is designed so that the o-ring 36b is slightly compressed between the upper pin 38c and the spherical wall 36a.

In a similar fashion to the spherical joint 36, another spherical joint 40 is formed by the lower pin 38d, another o-ring 40b, and a spherical wall 40a formed in an insert located in the second link 42. This spherical joint 40 operates in much the same way as the spherical joint 36 does.

The second link 42 comprises a ball 42b rigidly mounted to the yoke 42a by a ball pin 42c. The ball 42b is held by a ball clip 42d which allows it to rotate. A bracket 42e secures ball clip 42d to the micromanipulator body 32. The bracket 42e has a slot 42f that constrains an end of ball pin 42c which protrudes from ball 42b. This arrangement allows the second link 42 to only rotate about a horizontal axis (shown by the direction arrows A and B) through the center of the ball 42b and another axis through the centerline of ball pin 42c.

Each of the two pin and clip connections 44 that allow the second link 42 to drive the mirror 46 consist of a mirror pin 44a attached by a bracket to the mirror 46, a support pin 44b mounted in an end of yoke 42a, and a spring clip 44c that biases mirror pin 44a against support pin 44b. One of the mirror pins 44a is straight while the other mirror pin 44a' has a notch in it that captures support pin 44b and spring clip 44c, thereby preventing side to side movement of the bottom of the mirror 46. This pin and clip arrangement constrains the mirror 46 to only rotation about two mutually perpendicular and intersecting axes: a first axis along a line between the center of rotation of ball joint 48 and the midpoint of an imaginary line between mirror pin 44a and mirror pin 44a'; and a second, horizontal axis through the center of the ball joint 48 in the direction indicated by the arrows A and B. As the second link 42 drives the mirror 46, the mirror pins 44a and 44a' are able to slide and pivot with respect to the support pins 44b, the spring clips 44c, and the yoke 42a.

The mirror is mounted on its upper end by the ball joint 48 which consists of a pivot ball member 48a rigidly mounted to the body 32, and a pivot clip 48b which captures the pivot ball 48a and slides onto and grips the top of the mirror 46. The mirror 46 can easily be removed from the micromanipulator 30 for cleaning or replacement by pulling up on the pivot clip 48b until it disengages the pivot ball member 48a; the mirror 46 can then be lifted up and out through the top of the body 32.

FIG. 2 shows (in phantom lines) the envelope of the laser beam 12 passing through a lens (also shown in phantom lines) of the focusing optics 16 and reflecting off of the mirror 46 towards the target 24 on the patient. The mirror 46 of the preferred embodiment has a reflective coating over its lower side for reflecting the infrared radiation of the surgical beam, and a thin, aluminum, elliptical shaped spot in the center of its lower side for reflecting the visible light of the aiming beam. The aluminum spot is made as small as possible (about 8 mm wide) so as to obstruct as little of the surgeon's view as possible. It is envisioned that the spot may be eliminated completely with the development of new mirror coatings. The surgeon's line of sight (not shown) is from the viewing optics above the micromanipulator 30, through the mirror 46, and down to the target area 24.

The operation of the novel linkage will now be described. When the joy stick handle 34a is moved in the direction of arrow A, the joy stick ball 34b rotates about its center, and, through the spherical joint 36, drives the upper pin 38c in the opposite direction, in the direction of arrow B. This forces the slider 38a and the lower pin 38d of the first link 38 along the main shaft 38b in the direction of arrow B. The lower pin 38d drives the second link 42 through the other spherical joint 40, causing the yoke 42a to pivot about the axis of the ball pin 42c which is constrained from translation by slot 42f. As the yoke 42a pivots, it drives the mirror 46 through the two sets of pin and clip connections 44 causing the mirror to pivot about its ball joint 48. The motion of the mirror 46 is about an axis that runs through the center of the ball joint 48 to the mid-point of an imaginary line connecting the mirror pin 44a with the pin 44a'. This causes the laser beam 12 at target 24 to move in the direction of arrow A, the same direction the joy stick handle 34a was moved in. The distance that the laser beam 12 moves depends on the amount of movement of the joy stick handle 34a, the predetermined amplification or reduction ratio of the linkage and mirror arrangement, and the distance from the mirror to the target 24. As an example of this movement in the preferred embodiment, when the system is set up with a 300 mm set of focusing optics 16 and viewing optics 18, and the joy stick handle 34a is moved from an extreme position in the direction of arrow B to an extreme position in the direction of arrow A, the laser beam moves roughly 46 mm on the patient in the direction of arrow A.

When the joy stick handle 34a is moved in the direction of arrow C, the joy stick ball 34b rotates about its center, and, through the spherical joint 36, drives the upper pin 38c in the opposite direction, as shown by arrow D. This forces the slider 38a and the lower pin 38d of the first link 38 to rotate about the main shaft 38b. The lower pin 38d, moving in the direction C, drives the second link 42 through the other spherical joint 40, causing the yoke 42a to rotate about a horizontal axis through the center of the ball 42b and perpendicular to the ball pin 42c because ball pin 42b is constrained to travel in a vertical path by slot 42f. As the yoke 42a rotates, it drives the mirror 46 through the two sets of pin and clip connections 44 causing the mirror to pivot about its ball joint 48 in an upwardly direction. The motion of the mirror 46 is about a horizontal axis passing through the center of the ball joint 48 in the direction of A and B. This causes the laser beam 12 at target 24 to move in the direction of arrow C, the same direction the joy stick handle 34a was moved in.

Similarly, when the joy stick handle 34a is moved in the direction B or D, the linkage and mirror operate in a manner that is opposite to that described above for directions A and C, respectively. It will be appreciated by one skilled in the art that a movement of the joy stick handle 34a in direction that is not purely in one of the four directions A, B, C, or D is equivalent to a combination of movements in two of these directions.

In order to shorten the height of the micromanipulator 30 in the preferred embodiment, the ball 42b of the second link 42 is located above the bottom of the mirror 46 and the ball 48a of the ball joint 48 is located below the top the mirror 46. This means that the inclined axis of rotation does not lie in the same plane as the mirror 46 and is less than 45 degrees above horizontal.

It can be seen by study of the first link 38 that changing the working length of the upper pin 38c and/or the lower pin 38d will affect the motion in the vertical direction (shown by arrows C and D), but will not affect the motion in the horizontal direction (shown by arrows A and B). To achieve equal movements of the laser beam 12 in the horizontal and vertical directions for equal movements of the joy stick, the length of the upper pin 38c with respect to the lower pin 38d is set such that the mirror 46 (when set at a 45 degree angle) rotates the square root of two (approximately 1.41) times as far about an axis inclined at 45 degrees as it does about a horizontal axis. Because of the complex nature of the linkage in the preferred embodiment of the invention, the ratio between the lengths of the upper and lower pins was found by trial and error using computer models and prototypes. In the preferred embodiment the working length (the distance from the center of the lower o-ring 40b to the centerline of the main shaft 38b) of the lower pin 38d is 1.36 times as long as that of the upper pin 38c. It should be noted that although the vertical input motion (shown by arrows C and D) is being amplified approximately 36% with respect to the horizontal input motion (shown by arrows A and B) by the first link 38, the horizontal output rotation of the mirror 46 is amplified approximately 41% (the square root of two) with respect to the rotation in the vertical motion direction by the entire linkage. This is due to the fact that the horizontal mirror axis (rotated about when the mirror directs the laser beam in the vertical motion directions C and D) does not pass through the center of the mirror. Because this horizontal mirror axis instead passes through the center of the ball joint 48 and the mirror 46 is driven at its opposite end, the length of the mirror 46 determines the amount of amplification in the vertical motion that should be provided by the first link 38. In other words, the longer the mirror 46 is in this mirror mounting arrangement, the longer the lower pin 38d will need to be to provide the proper relationship between the outputs of motion in the two axes of the mirror.

The particular dimensions of the linkage have been selected such that ratio of the movement of the laser beam on the target in two dimensions is equivalent to the ratio of the movement in two dimensions of the joy stick. In this manner, if the joy stick is moved in a circular pattern, the beam is translated in a circle at the target.

Nominal mirror angles other than 45 degrees may be used with the present invention. For angles greater than 45 degrees to the laser beam, the ratio of relative angular rotation of the two mirror axes would be less than the square root of two. Conversely, for mirror angles less than 45 degrees, the ratio would be greater than the square root of two.

In the preferred embodiment, the range of motion of the joy stick 34a is 15 degrees in any direction from its center position. This range of input motion produces roughly a 2.5 degree output motion of the mirror about its horizontal axis and roughly a 3.5 degree output motion about a perpendicular inclined axis through the mirror. These output rotations of the mirror guide the laser beam trough a range of motion that is 5 degrees in any direction from the center position.

Another design feature of the present invention is its inherent ability to allow the angle of the entire joy stick assembly 34 to be changed without affecting the kinematics of the linkage. In the preferred embodiment, as shown in FIG. 2, the joy stick 34 is positioned 25 degrees from vertical. A particular surgical procedure may be easier to perform with a joy stick angle other than 25 degrees. This can be changed, for example, to 45 degrees by replacing the straight joy stick body 34c with one that has a 20 degree bend in it at the main shaft 38b, and by replacing the slider 38a with one that positions the upper pin 38c and the lower pin 38d 160 degrees apart instead of 180 degrees. The slider can be manufactured with more than one pair of pin receiving holes in it for this purpose, with the holes of each pair situated at different angles. Then the only part that needs to be manufactured and stocked for a different joy stick angle is the joy stick housing 34c. The joy stick assembly 34 is easily removed (and replaced) from the micromanipulator body 32 by loosening three set screws (not shown) and pulling the joy stick assembly 34 away. The other parts of the micromanipulator 30, and the operation and kinematics of the linkage will be identical regardless of the angle configuration of the joy stick assembly.

Figure 3:
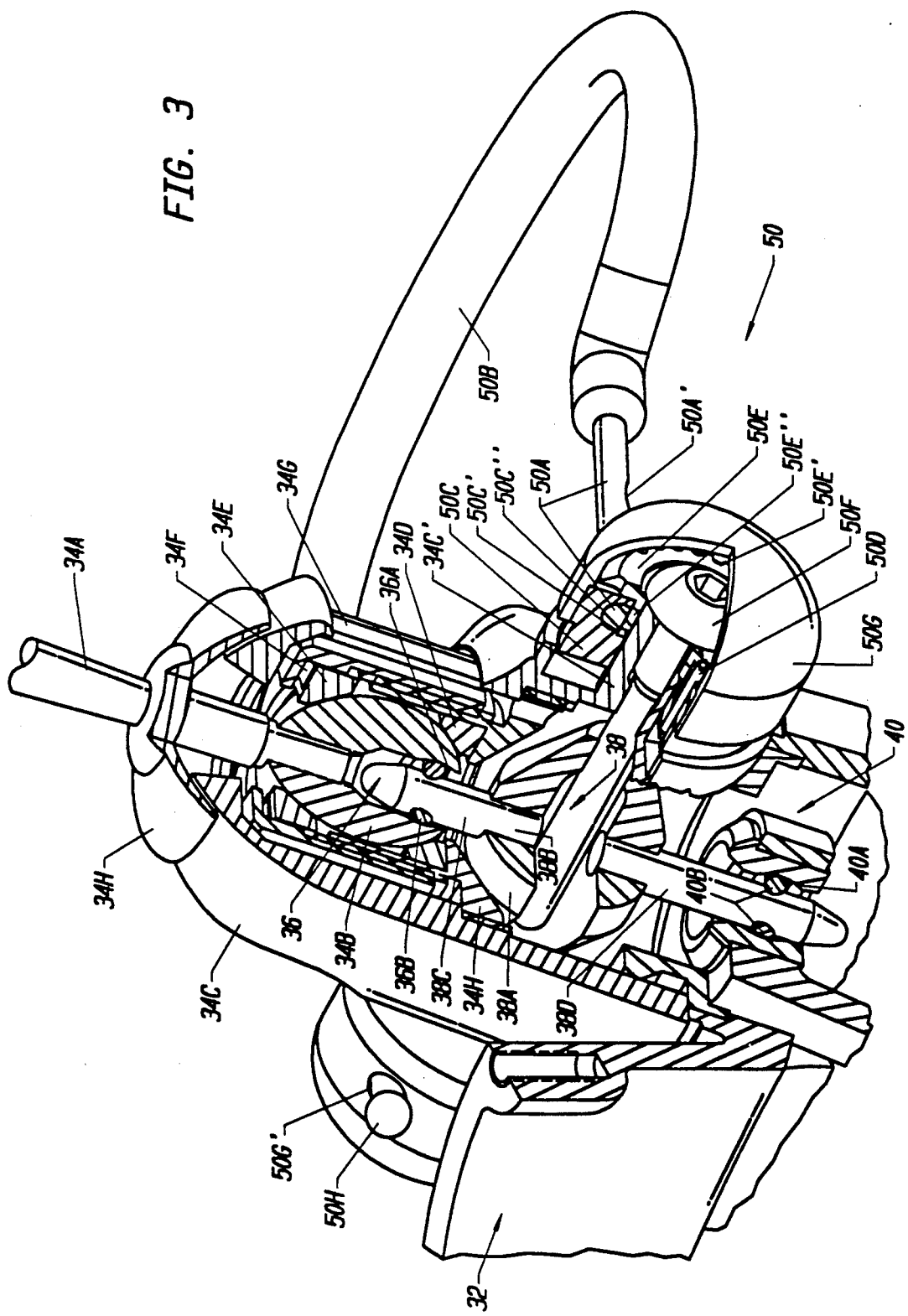
FIG. 3 is an enlarged view of a portion of FIG. 1 showing the features of the adjustable hand rest.

An additional feature of the new micromanipulator 30 is an adjustable hand rest 50 that can be fully retracted out of the way when not being used. Referring now to FIG. 3, the hand rest 50 is made up of a generally U-shaped bale 50a that is partially covered by an elastomer 50b, such as a silicone tubing, and connects at both ends to the joy stick body 34c through identical adjustment mechanisms. Each adjustment mechanism includes a bale slider 50c, a detent plate 50e, two dowel pins 50d, a fastener 50f, and a cap 50g. The detent plate 50e is rigidly attached to a protruding cylindrical portion 34c' of the joy stick body 34c by the fastener 50f. The two pins 50d are rigidly attached to the bale slider 50c which slides on the protruding cylindrical portion 34c' between the detent plate 50e and the main portion of the joy stick body 34c. When the bale slider 50c is in its outermost position (as shown), the pins 50d attached to the bale slider 50c each engage in one of a series of notches 50e' on the outer periphery of the detent plate 50e, thereby preventing rotation of the bale slider 50c. The bale slider 50c has an axial counterbore 50c' that accepts a reduced diameter portion 50e'' of the detent plate 50e when the bale slider 50c is in its outermost position. The cap 50g is press fit over the bale slider 50c, thus enclosing the detent plate 50e. The bale slider 50c and cap 50g have aligning tangential bores 50c'' and 50g', respectively, transversely therethrough along a chord of the bale slider 50c such that the tangential bore 50c'' partially breaks into the counterbore 50c' of the bale slider 50c and is intruded upon by the reduced diameter portion 50e'' of the detent plate 50e when the bale slider 50c is in its outermost position. The tangential bores 50c'' and 50g' slidably accept an end of the bale 50a when the bale slider 50c (and therefore also the cap 50g) is in the innermost position. The ends of the bale 50a are retained in the adjustment assembly by end stop balls 50h that are attached to the ends of the bale 50a. Upon assembly, the bale 50a spring-loads the bale sliders 50c in an outward direction. Because the bale 50a interferes with the reduced diameter portion 50e'' of the detent plate 50e, the bale slider 50c is prevented from traveling into its outermost position. However, several scalloped portions 50a' on the bale 50a, when aligned properly in the bale slider 50c, allow the bale slider 50c to move into its outermost position, where its pins 50d engage the notches 50e' in the detent plate 50e, thereby preventing rotation of the bale slider 50c and the bale 50a. In this outermost position, longitudinal movement of the bale 50a is also prevented because the reduced diameter portions 50e'' of the detent plates 50e engage the scalloped portion 50a' of the bale 50a, locking the bale 50a in place.

In normal use, the adjustable hand rest 50 is locked in one position so that the surgeon can rest his hand upon it when operating the joy stick 34. To adjust the position of the hand rest 50, or to move it away from the joy stick handle 34a and out of the way, the surgeon squeezes the two sides of the bale 50a together. This action moves the two bale slides 50c into their innermost positions, thereby disengaging the four pins 50d from the notches 50e' in the detent plates 50e, and moving a pair of scalloped portions 50a' of the bale 50a out of engagement with the reduced diameter portions 50e'' of the detent plates 50e. The surgeon is then free to rotate the bale 50a up or down and push it in or pull it out to the desired position. After releasing the squeezing force on the bale 50a, the surgeon then slightly moves the bale 50a in or out and rotates it until a set of scallops 50a' engage the reduced diameter portions 50e'' of the detent plates 50e and the pins 50d drop into another set of notches 50e'. The bale 50a then becomes locked in the new working position or is out of the way up against the micromanipulator body 32.

With the joy stick handle 34a and hand rest bale 50a removed, the approximate overall dimensions of the micromanipulator 30 in the preferred embodiment are: 4.5 inches in length; 3 inches in width; and 2.75 inches in height.

Standard engineering materials, known by those skilled in the art, are used for the various components of the micromanipulator 30. The exterior surfaces of the micromanipulator body 32, the joy stick body 34b, the adjustable joy stick load nut 34g, and the adjustable hand rest caps 50g are all coated with a standard paint in the preferred embodiment.

A grease, such as "Apiezon M" manufactured by Apiezon Products Limited, 4 York Road, London S.E. 1, is used to lubricate parts such as the joy stick ball seat 34d and load pad 34e, the spherical joints 36 and 40, the slider 38a of the first link 38, and the ball 42b and pin 42c joint of the second link 42. The upper ball joint 48 of the mirror 46 and the pin and clip connections 44 are left unlubricated.

The above embodiment, detailed descriptions, and drawings are meant for illustrative purposes only. As many possible different embodiments of this invention may be made without departing from the spirit and scope thereof, it is to be understood that the invention is not limited to the specific embodiment described and illustrated herein except as defined in the appended claims.

What is claimed as the invention is:

1. A linkage assembly for a surgical laser manipulating apparatus, said linkage permitting spherical motion, comprising:
   a first pin member;
   a second member having a spherical recess; and
   an o-ring positioned within said recess receiving said pin member, said recess acting to constrain said o-ring and said pin member from transverse motion but allowing said o-ring and said pin member to pivot with respect to said recess in any transverse direction, and said recess acting in cooperation with said o-ring allowing axial translation of said pin member with respect to said recess.

2. The linkage assembly recited in claim 1, wherein said o-ring remains under a substantially uniform compression between said first pin member and said second member as said pin member moves with respect to said second member, thereby reducing backlash and hysteresis and providing a more uniform motion of said linkage assembly.

* * * * *

UNITED STATES PATENT AND TRADEMARK OFFICE
CERTIFICATE OF CORRECTION

PATENT NO.    : 5,304,174                                                Page 1 of 1
DATED         : April 19, 1994
INVENTOR(S)   : Estrada et al.

It is certified that error appears in the above-identified patent and that said Letters Patent is hereby corrected as shown below:

Title page,
Item [21], Appl. No., please change to -- 08/100,722 --.
Item [62], please delete "Division of Ser. No. 841,427, Feb 26, 1992, Pat No. 5,207,380." and insert in lieu of -- Division of US Ser. No. 841,426, filed February 26, 1992, Now US Patent 5,257, 992 --

Signed and Sealed this

Tenth Day of June, 2003

JAMES E. ROGAN
*Director of the United States Patent and Trademark Office*